United States Patent
Ku

(10) Patent No.: US 6,613,016 B1
(45) Date of Patent: Sep. 2, 2003

(54) SAFETY HYPODERMIC SYRINGE

(76) Inventor: Jen Chuan Ku, 1F, No. 792, Hsing Fu Rd., Hsinchuang City, Taipei Hsien (TW)

( * ) Notice: Subject to any disclaimer, the term of this patent is extended or adjusted under 35 U.S.C. 154(b) by 0 days.

(21) Appl. No.: 10/347,200

(22) Filed: Jan. 21, 2003

(51) Int. Cl.[7] .............................. A61M 5/00; A61M 5/32
(52) U.S. Cl. ........................................ 604/110; 604/195
(58) Field of Search ................................ 604/110, 195, 604/196, 208–210, 225, 263

(56) References Cited

U.S. PATENT DOCUMENTS

| | | | | |
|---|---|---|---|---|
| 5,098,402 A | * | 3/1992 | Davis | 604/195 |
| 5,176,640 A | * | 1/1993 | Nacci et al. | 604/110 |
| 5,221,262 A | * | 6/1993 | Kite | 604/110 |
| 5,382,235 A | * | 1/1995 | Sak | 604/110 |
| 5,405,327 A | * | 4/1995 | Chen | 604/110 |
| 5,496,278 A | * | 3/1996 | Buff | 604/110 |
| 5,531,705 A | * | 7/1996 | Alter et al. | 604/110 |
| 5,533,975 A | * | 7/1996 | Lu | 604/195 |
| 5,693,023 A | * | 12/1997 | Adams | 604/110 |
| 5,820,605 A | * | 10/1998 | Zdeb et al. | 604/195 |
| 5,899,887 A | * | 5/1999 | Liu | 604/195 |
| 6,010,486 A | * | 1/2000 | Carter et al. | 604/195 |
| 6,193,695 B1 | * | 2/2001 | Rippstein, Jr. | 604/195 |
| 6,461,328 B2 | * | 10/2002 | Wang et al. | 604/110 |

* cited by examiner

*Primary Examiner*—Sharon Kennedy
(74) *Attorney, Agent, or Firm*—Rosenberg, Klein & Lee

(57) ABSTRACT

A safety hypodermic syringe having a flexible safety cap covered on a hollow stopper around the arrowhead tip of the plunger, such that liquid medicine is completely forced out of the barrel through the needle cannula before forcing the arrowhead tip of the plunger into engagement with the connector holding the needle hub and the needle cannula for enabling the needle cannula to be received inside the barrel after the service of the safety hypodermis syringe.

5 Claims, 10 Drawing Sheets

SAFETY HYPODERMIC SYRINGE

BACKGROUND OF THE INVENTION

1. Field of the Invention

The present invention relates to the installation of a hypodermic syringe and, more particularly, to a disposable safety hypodermic syringe.

2. Description of the Related Art

In order to prevent possible contamination after injection, safety hypodermic syringes are commonly used. A safety hypodermic syringe keeps the needle cannula concealed inside the barrel after its service. FIG. 1 illustrates a safety hypodermic syringe according to the prior art. According to this design, the safety hypodermic syringe comprises a barrel 60, an annulus connector 61 inserted into the inside of the barrel 60 and stopped inside the front end of the barrel 60, a needle hub 62 fastened to the connector 61 to hold a needle cannula outside the barrel 60, and a plunger 63 fitting the barrel 60. The plunger 63 has a front end fixedly mounted with a stopper, which has an arrowhead tip 64 for engaging the connector 61 for enabling the connector 61 and the needle hub 62 to be pulled backwards to the inside of the barrel 60 after the service of the safety hypodermic syringe. This structure of safety hypodermic syringe is still not satisfactory in function. When the plunger 63 moved forwards to force the liquid medicine 65 out of the barrel 60 through the needle cannula in the needle hub 62, the arrowhead tip 64 of the stopper is forced into engagement with the connector 61. At this time, the plunger 63 is prohibited from forward movement, and a residual amount of liquid medicine 65 left in the gap between the connector 61 and the stopper, resulting in an insufficient dosage give to the patient.

Therefore, it is desirable to have a safety hypodermic syringe that eliminates the aforesaid problem.

SUMMARY OF THE INVENTION

The present invention has been accomplished under the circumstances in view. It is therefore the main object of the present invention to provide a safety hypodermic syringe, which enables the full dosage of liquid medicine to be completely applied to the patient after its service. It is another object of the present invention to provide a safety hypodermic syringe, which enables the needle cannula to be concealed inside the barrel and the plunger separated from the barrel after its service.

To achieve these and other objects of the present invention, the safety hypodermic syringe comprises a body unit, the body unit comprising a barrel, a hollow cylindrical connector inserted into the barrel and stopped inside a front end of the barrel, and a needle hub fastened to the connector and holding a needle cannula outside the barrel; and a plunger unit, the plunger unit comprising a stepped plunger fitting the barrel, the stepped plunger having a front tip, a hollow stopper mounted on the stepped plunger around the front tip, and a flexible safety cap capped on the hollow stopper, the flexible safety cap having a locating groove of smoothly arched cross section extended around the periphery thereof; wherein the hollow cylindrical connector has a plurality of inside annular flanges adapted to secure the needle hub to the connector; the stepped plunger has an annular groove extended around the periphery thereof near the front tip; the hollow stopper has an inside annular flange forced into engagement with the annular groove of the stepped plunger; the front tip is forced through the flexible safety cap into engagement with the inside annular flanges of the hollow cylindrical connector when the plunger continuously forced forward after a forward stroke of the flexible safety cap and the hollow stopper with the plunger to expel a liquid medicine out of the barrel through the needle cannula, for enabling the needle hub and the needle cannula to be moved with the connector and the flexible safety cap and the hollow stopper backwards to the inside of the barrel upon a back stroke of the plunger; the front tip is breakable when the plunger biased by an external force after the connector has been moved with the plunger backwards to a rear end of the barrel.

DETAILED DESCRIPTION OF THE PREFERRED EMBODIMENT

Figure 1:
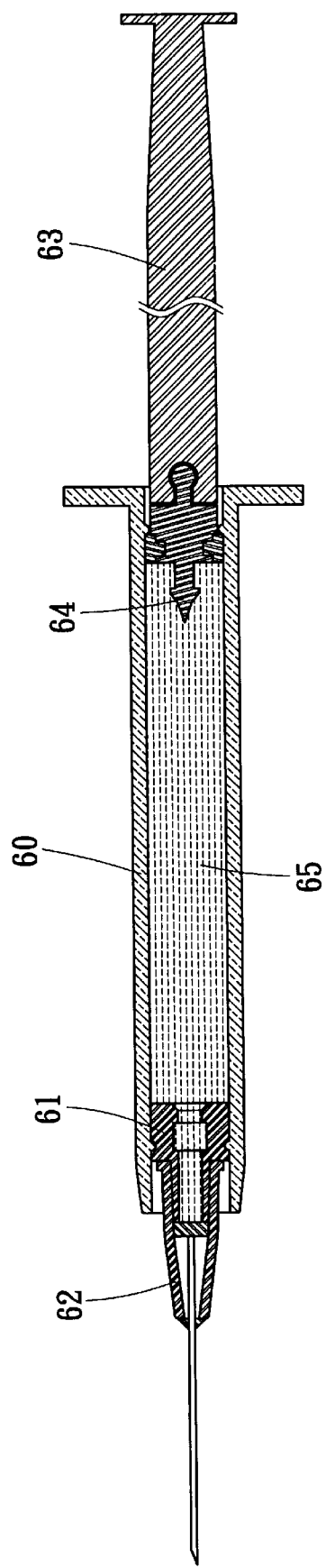
FIG. 1 is a sectional view of a safety hypodermic syringe according to the prior art.
Figure 2:
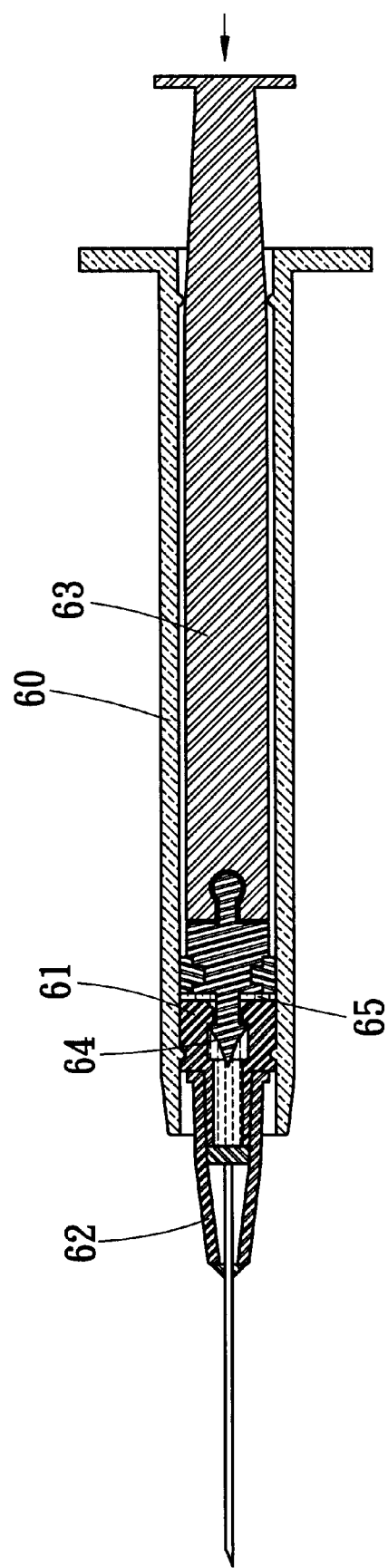
FIG. 2 is an applied view in section of the prior art safety hypodermic syringe.
Figure 3:
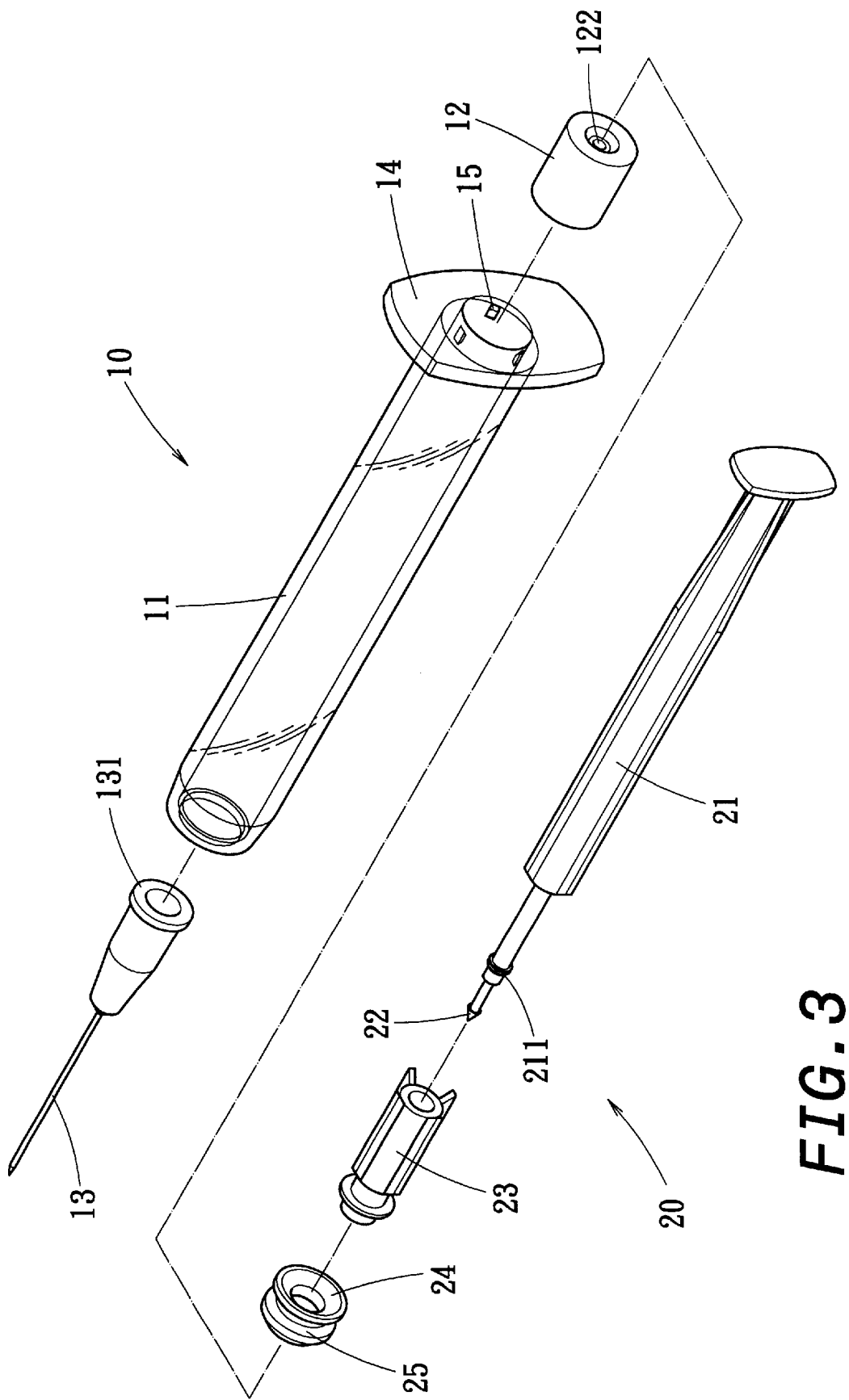
FIG. 3 is an exploded view of a safety hypodermic syringe according to the present invention.
Figure 4:
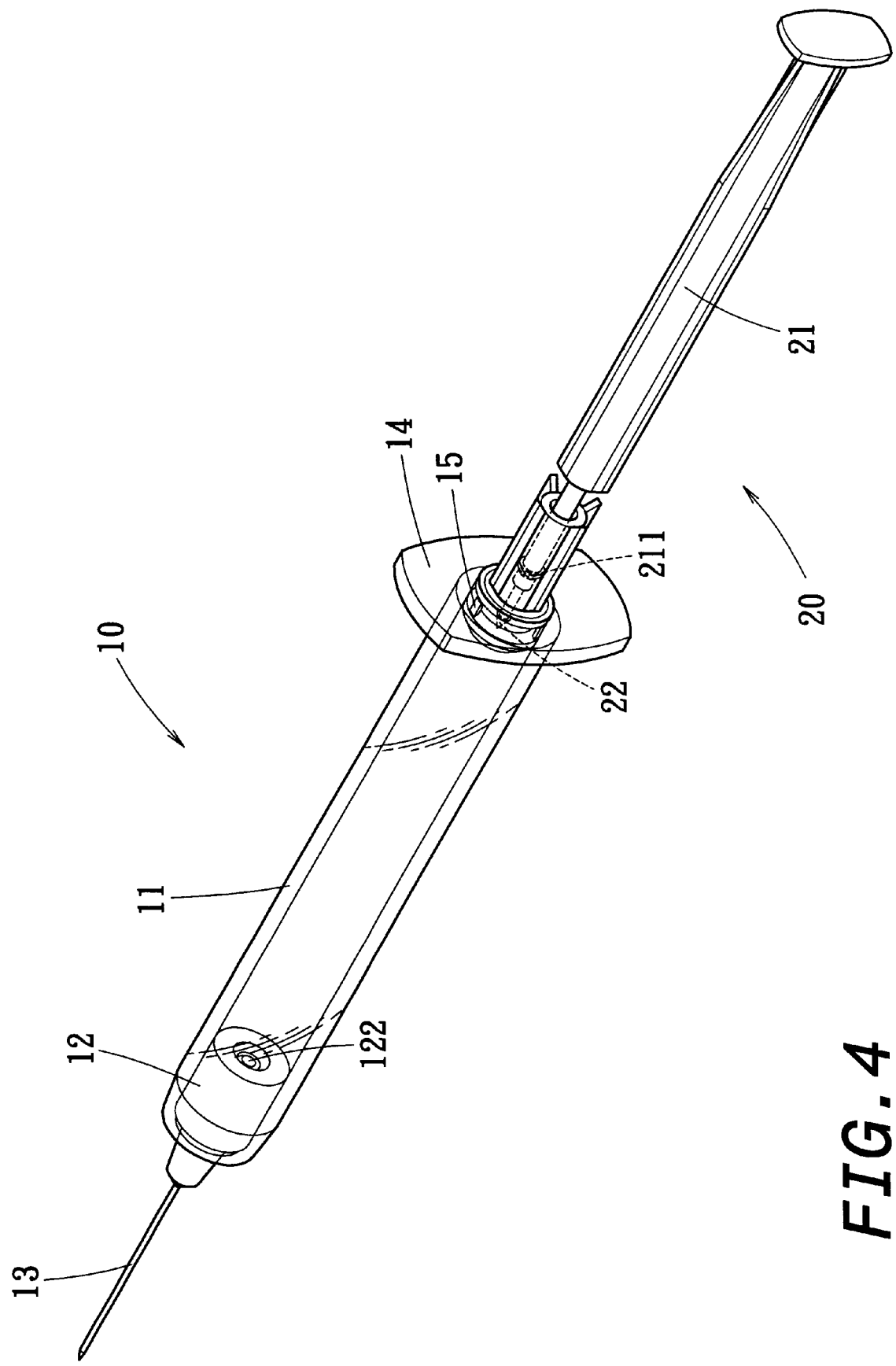
FIG. 4 is a perspective assembly view of the safety hypodermic syringe according to the present invention.
Figure 5:
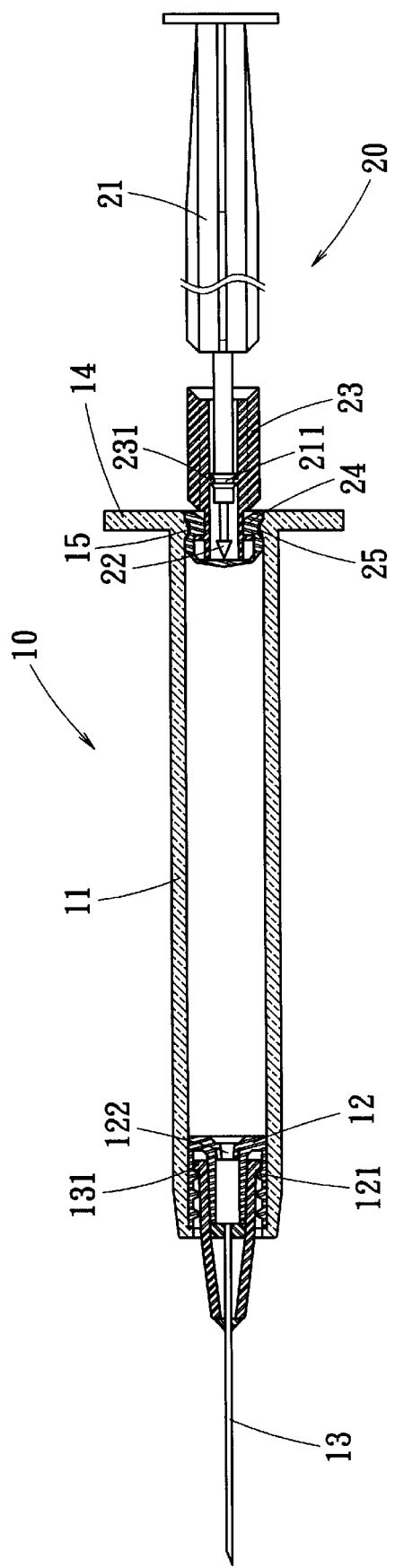
FIG. 5 is a sectional view of the safety hypodermic syringe according to the present invention.
Figure 6:
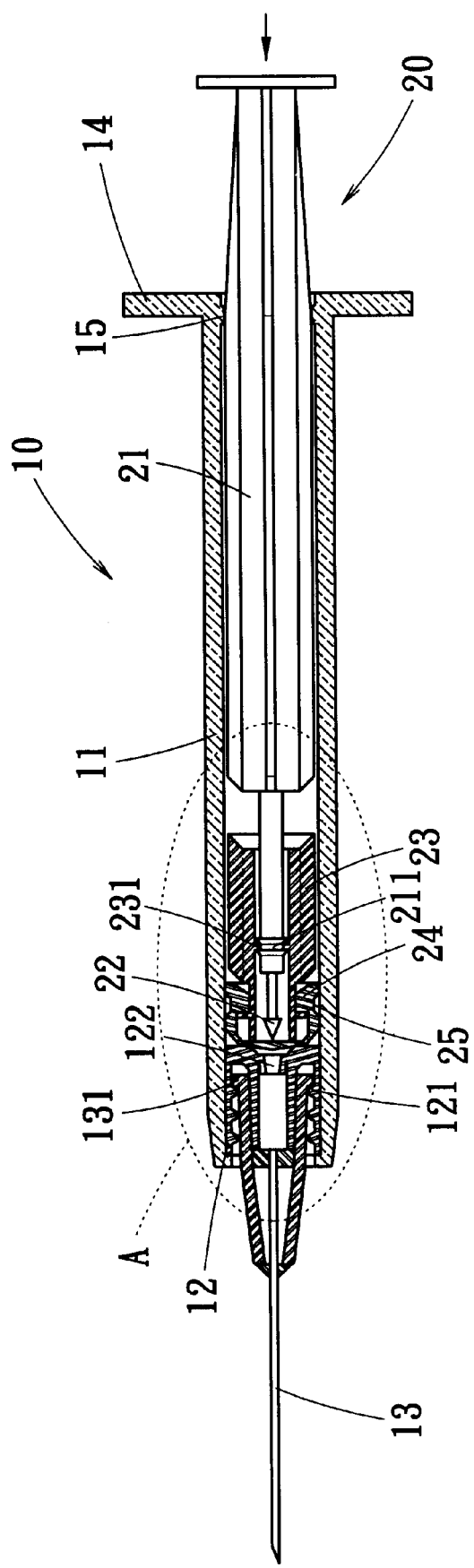
FIG. 6 is another sectional view of the present invention, showing the flexible safety cap stopped at the connector.
Figure 6A:
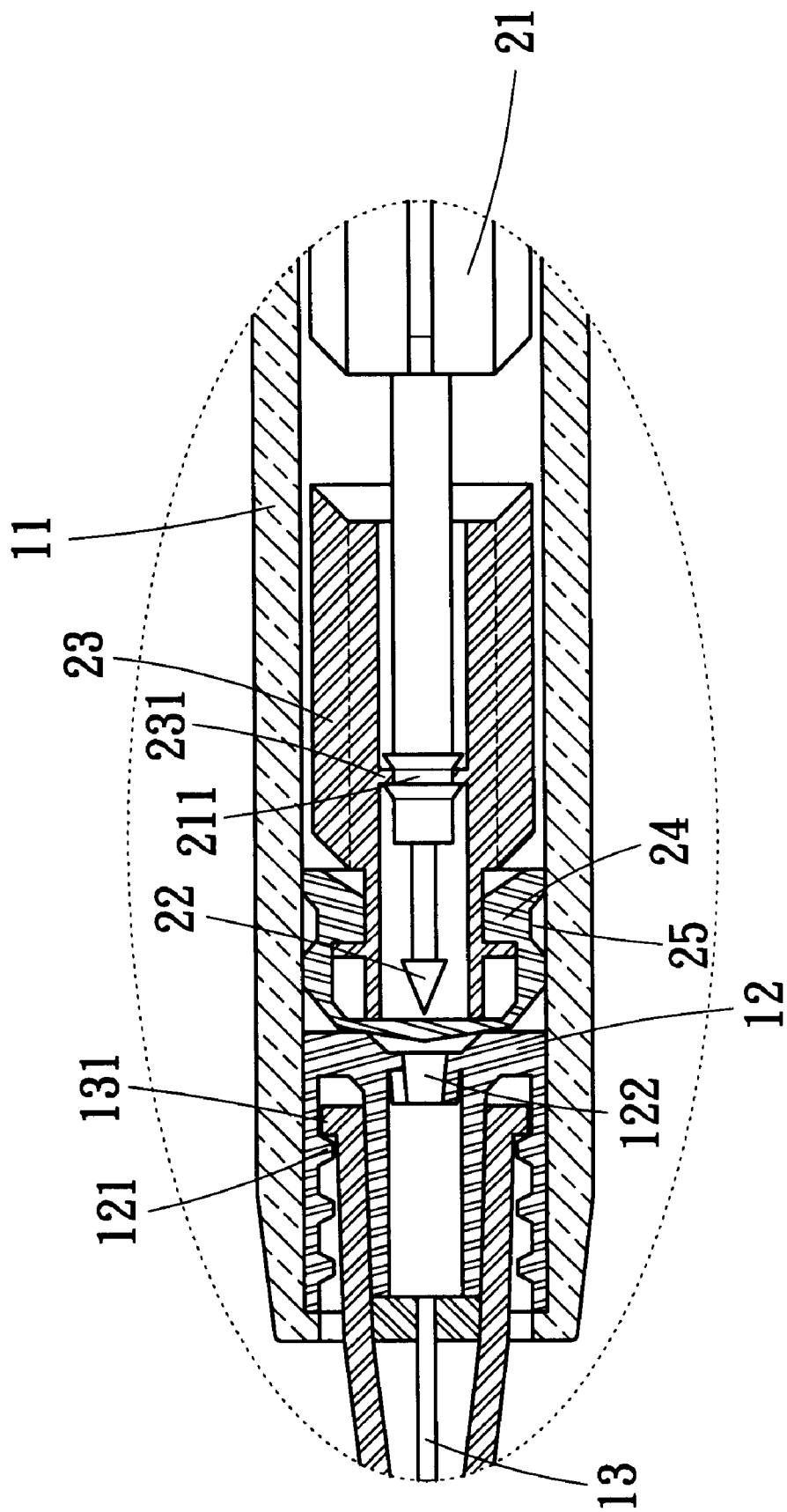
FIG. 6A is an enlarged view of a part of FIG. 6.
Figure 7:
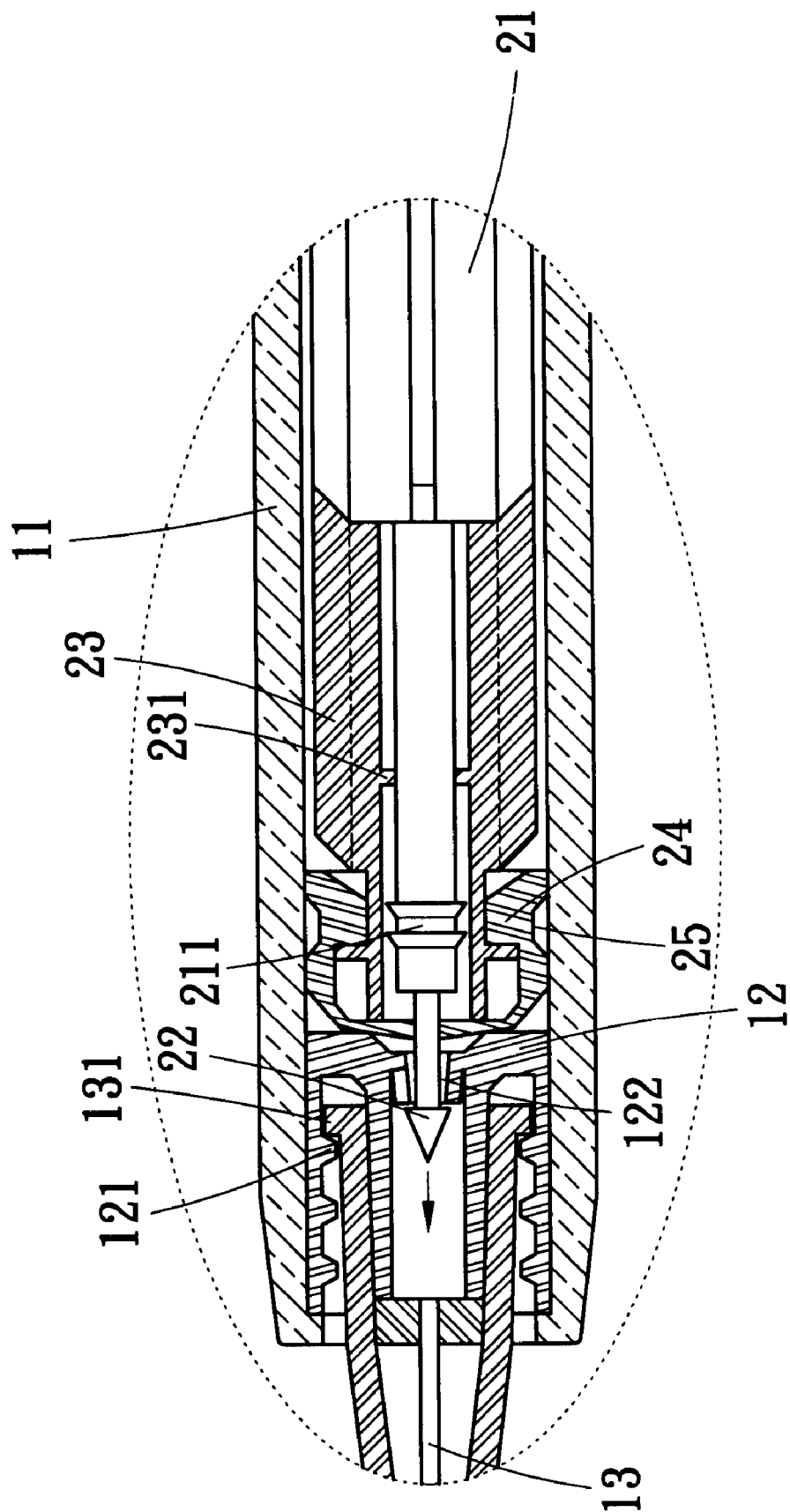
FIG. 7 is similar to FIG. 6A but showing the plunger continuously forced forwards, the arrowhead tip of the plunger passed through the flexible safety cap and engaged into the connector.
Figure 8:
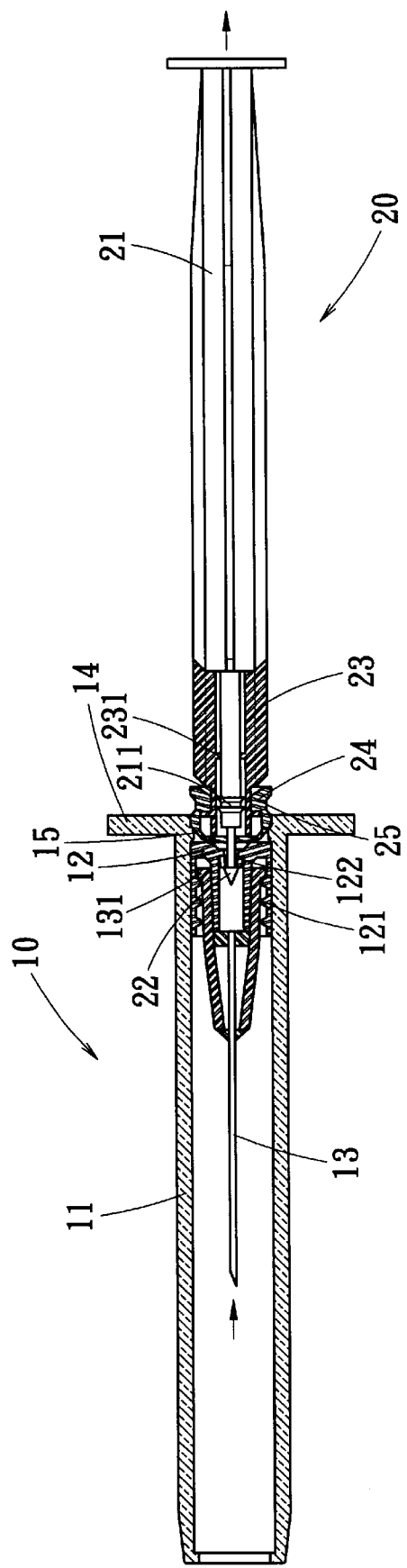
FIG. 8 illustrates the needle nub with the needle cannula moved with the connector and the plunger to the rear end of the barrel according to the present invention.
Figure 9:
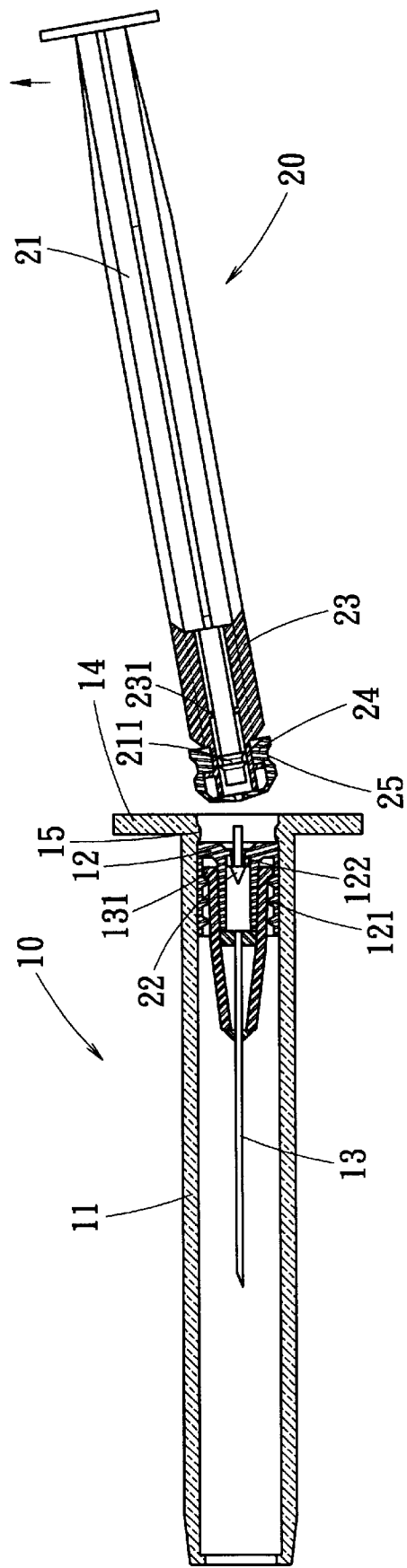
FIG. 9 illustrates the plunger unit separated from the body unit, the broken arrowhead tip left with the connector and the needle hub and the needle cannula inside the barrel.

Referring to FIGS. 3~5, a safety hypodermic syringe is show comprised of a body unit 10 and a plunger unit 20. The body unit 10 is comprised of a barrel 11, a connector 12, and a flanged needle hub 131 holding a needle cannula 13. The barrel 11 has a finger flange 14 at one end, and a plurality of raised portions 15 protruded from the inside wall corresponding to the finger flange 14. The connector 12 is a hollow cylindrical member inserted into the barrel 11 and stopped at one end of the barrel 11 remote from the finger flange 14, having a plurality of inside annular flanges 121 and a conical orifice 122 in the rear end. The plunger unit 20 comprises a stepped plunger 21, the stepped plunger 21 having an arrowhead tip 22 and an annular groove 211 around the periphery near the arrowhead tip 22, a hollow stopper 23 mounted on the arrowhead tip 22 of the stepped plunger 21, the stopper 23 having an inside annular flange 231 forced into engagement with the annular groove 211, and a flexible safety cap 24 capped on the front end of the stopper 23. The flexible safety cap 24 has a locating groove 25 of smoothly arched cross section extended around the periphery. During the assembly process of the safety hypodermic syringe, the dome-like flexible safety cap 24 is inserted with the stopper 23 and the plunger 21 into the barrel 11.

Referring to FIGS. 6~9, the arrowhead tip 22 of the plunger 21 is received inside the stopper 23 and the flexible safety cap 24 is capped on the front end of the stopper 23, the arrowhead tip 22 is prohibited from touching the connector 12 in the front end of the barrel 11 before the liquid medicine has been completely forced out of the barrel 11 through the needle cannula 13. When the user continuously pushing the plunger 21 forwards after the flexible safety cap 24 touched the rear side of the needle hub 131 (after the liquid medicine has been completely forced out of the barrel 11 through the needle cannula 13), the arrowhead tip 22 is forced through the flexible safety cap 24 into the conical orifice 122 of the connector 12 and then into engagement with the inside annular flanges 121 of the connector 12. When the user pulling the plunger 21 backwards at this time, the connector 12 and the needle hub 131 with the needle cannula 13 are moved backwards with the arrowhead tip 22 of the plunger 21 toward the rear side of the barrel 11. When continuously pulling the plunger 21 backwards, the locating groove 25 of the flexible safety cap 24 is forced into engagement with the raised portions 15 of the barrel 11, thereby causing the flexible safety cap 24 to be stopped in the rear end of the barrel 11. At this time, the user can bias the plunger 21 to break the arrowhead tip 22, keeping the broken arrowhead tip 22 left in the connector 12 inside the barrel 11, and therefore the plunger unit 20 is separated from the body unit 10, and the needle hub 131 with the needle cannula 13 and the connector 12 with the broken arrowhead tip 22 are kept inside the barrel 11 after the service of the safety hypodermic syringe.

As indicated above, the arrangement of the stopper 23 and the flexible safety cap 24 prohibits the arrowhead tip 22 of the plunger 21 from engaging the connector 12 before empty of liquid medicine. Further, the engagement between the locating groove 25 of the flexible safety cap 24 and the raised portions 15 of the barrel 11 enables the arrowhead tip 22 of the plunger 21 to be easily broken when biasing the plunger 21 after the plunger 21 has been pulled out of the barrel 11 after the service of the safety hypodermic syringe.

A prototype of safety hypodermic syringe has been constructed with the features of the annexed drawings of FIGS. 3~9. The safety hypodermic syringe functions smoothly to provide all of the features discussed earlier.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A safety hypodermic syringe comprising:
    a body unit, said body unit comprising a barrel, a hollow cylindrical connector inserted into said barrel and stopped inside a front end of said barrel, and a needle hub fastened to said connector and holding a needle cannula outside said barrel; and
    a plunger unit, said plunger unit comprising a stepped plunger fitting said barrel, said stepped plunger having a front tip, a hollow stopper mounted on said stepped plunger around said front tip, and a flexible safety cap capped on said hollow stopper, said flexible safety cap having a locating groove of smoothly arched cross section extended around the periphery thereof;
    wherein said hollow cylindrical connector has a plurality of inside annular flanges adapted to secure said needle hub to said connector; said stepped plunger has an annular groove extended around the periphery: thereof near said front tip; said hollow stopper has an inside annular flange forced into engagement with the annular groove of said stepped plunger; said front tip is forced through said flexible safety cap into engagement with the inside annular flanges of said hollow cylindrical connector when said plunger continuously forced forward after a forward stroke of said flexible safety cap and said hollow stopper with said plunger to expel a liquid medicine out of said barrel through said needle cannula, for enabling said needle hub and said needle cannula to be moved with said connector and said flexible safety cap and said hollow stopper backwards to the inside of said barrel upon a back stroke of said plunger; said front tip is breakable when said plunger biased by an external force after said connector has been moved with said plunger backwards to a rear end of said barrel.

2. The safety hypodermic syringe as claimed in claim 1, wherein said hollow cylindrical connector has a conical orifice in one end thereof through which said front tip of said plunger is forced into engagement with the inside annular flanges of said hollow cylindrical connector.

3. The safety hypodermic syringe as claimed in claim 1, wherein said front tip of said plunger is shaped like an arrowhead.

4. The safety hypodermic syringe as claimed in claim 1, wherein said flexible safety cap has a dome-like shape and is capped on a front end of said hollow stopper.

5. The safety hypodermic syringe as claimed in claim 1, wherein said flexible safety cap has a locating groove of smoothly arched cross section extended around the periphery thereof; said plunger has at least one raised portion protruded from an inside wall near a rear end thereof and adapted to engage the locating groove of said flexible safety cap for enabling said front tip to be broken from said plunger when biasing said plunger.

* * * * *